(12) United States Patent
Rovegno

(10) Patent No.: US 7,074,182 B2
(45) Date of Patent: Jul. 11, 2006

(54) VIDEOENDOSCOPE

(75) Inventor: Jean Rovegno, La Ciotat (FR)

(73) Assignee: Tokendo, La Ciotat (FR)

( * ) Notice: Subject to any disclaimer, the term of this patent is extended or adjusted under 35 U.S.C. 154(b) by 0 days.

(21) Appl. No.: 10/757,213

(22) Filed: Jan. 13, 2004

(65) Prior Publication Data

US 2004/0204628 A1    Oct. 14, 2004

(30) Foreign Application Priority Data

| Jan. 17, 2003 | (FR) | ................................. 03 00547 |
| Jan. 28, 2003 | (FR) | ................................. 03 00916 |
| Jan. 31, 2003 | (FR) | ................................. 03 01134 |
| May 22, 2003 | (FR) | ................................. 03 06180 |

(51) Int. Cl.
*A61B 1/04* (2006.01)

(52) U.S. Cl. ...................................... 600/131; 600/132

(58) Field of Classification Search ................ 600/109, 600/118, 131–132, 146, 160
See application file for complete search history.

(56) References Cited

U.S. PATENT DOCUMENTS

| 3,481,557 | A |  | 12/1969 | Miller |  |
| 4,712,133 | A |  | 12/1987 | Kikuchi |  |
| 4,913,369 | A |  | 4/1990 | Lia et al. |  |
| 4,941,454 | A | * | 7/1990 | Wood et al. | ................. 600/149 |
| 4,982,725 | A | * | 1/1991 | Hibino et al. | ................ 600/117 |
| 5,373,317 | A | * | 12/1994 | Salvati et al. | .................. 348/65 |
| 5,549,542 | A | * | 8/1996 | Kovalcheck | ................ 600/146 |
| 5,630,783 | A | * | 5/1997 | Steinberg | .................... 600/158 |
| 5,658,238 | A | * | 8/1997 | Suzuki et al. | ................ 600/150 |
| 5,873,814 | A | * | 2/1999 | Adair | .......................... 600/109 |
| 5,928,137 | A | * | 7/1999 | Green | .......................... 600/160 |
| 6,066,089 | A | * | 5/2000 | Costello et al. | ............. 600/102 |
| 6,126,591 | A |  | 10/2000 | McGarry et al. |  |
| 6,315,712 | B1 | * | 11/2001 | Rovegno | ..................... 600/109 |
| 6,540,670 | B1 | * | 4/2003 | Hirata et al. | ................. 600/152 |
| 2002/0026096 | A1 |  | 2/2002 | Motoki et al. |  |
| 2002/0032365 | A1 |  | 3/2002 | Hasegawa et al. |  |
| 2003/0060681 | A1 | * | 3/2003 | Yokota | ........................ 600/117 |
| 2004/0133075 | A1 | * | 7/2004 | Motoki et al. | ............... 600/131 |

FOREIGN PATENT DOCUMENTS

| DE | 44 15 116 A | 11/1995 |
| EP | 0 587 514 A1 | 3/1994 |
| FR | 2 785 132 | 4/2000 |
| GB | 2 345 606 A | 7/2000 |
| JP | 03053771 | 7/1991 |
| JP | 2002034912 | 5/2002 |
| WO | WO 97/15144 | 4/1997 |
| WO | WO 97/41767 | 11/1997 |

* cited by examiner

*Primary Examiner*—John Leubecker
*Assistant Examiner*—Philip R. Smith
(74) *Attorney, Agent, or Firm*—Merchant & Gould P.C.

(57) ABSTRACT

A videoendoscope comprising an inspection probe comprising an inspection tube and a distal endpiece secured to one end of the inspection tube and housing an imaging device; a video processor for processing the electrical signal delivered by the imaging device and for generating a video signal; a control handle comprising a control unit secured to the inspection tube to control the video processor and a display unit secured to a side face of the control unit and including a display screen connected to the video processor; and an umbilical cable having one end secured to the control unit and having its other end connected to a light source and to an electrical power supply.

33 Claims, 9 Drawing Sheets

VIDEOENDOSCOPE

The present invention relates to a videoendoscope intended particularly but not exclusively to endoscopy for industrial purposes.

BACKGROUND OF THE INVENTION

The term "endoscope" is generally used to designate a flexible or rigid probe for inserting into a dark cavity and enabling its user to observe a target situated inside the cavity by means of an eyepiece. For this purpose, an endoscope includes a device for illuminating the target and an optical device for providing the user with an optical image of the target. The optical device comprises a distal objective lens, a rigid image transport device constituted by a series of lenses or a flexible image transport device constituted by an ordered bundle of optical fibers, and a proximal eyepiece through which the user can observe visually the image of the target. The lighting device is generally constituted by a bundle of lighting fibers with the distal end thereof being appropriately disposed close to the distal objective lens to light the target when the proximal end of the bundle is connected to a light generator.

The term "videoendoscope" is used to designate a flexible or rigid probe enabling its user to observe on a video screen the image of a target situated in a dark cavity. To this end, a videoendoscope generally comprises the following elements:

- a distal endpiece housing an optoelectronic device comprising in particular an objective lens and a charged-coupled device (CCD) sensor having a sensitive surface on which the objective lens forms an image of the target;
- a flexible inspection tube whose distal end is secured to the distal endpiece;
- a control handle secured to the proximal end of the inspection tube;
- a flexible umbilical cable for connection purposes whose distal end is secured to the control handle and whose proximal end is designed to be connected to an external unit containing a light generator and an electrical power supply;
- a bundle of lighting fibers housed in the umbilical cable, in the control handle, and in the inspection tube, with the distal end of the bundle housed in the distal endpiece serving to light the target when the proximal end of the bundle is connected to a light generator;
- a video processor electrically connected to the CCD sensor, with synchronization thereof being controlled as a function of the length of the electrical cable connecting it to the CCD sensor;
- a video screen connected to the video processor; and
- a control panel enabling the operation of the video processor and possibly also that of the video screen to be adjusted.

Flexible videoendoscopes also have an articulated bending section at the distal end enabling the distal endpiece of the probe to be steered, the control handle then generally including mechanical or electrochemical control means enabling the bending section to be actuated. The electromechanical control means for the distal bending section generally comprise two motors housed in the control handle and actuating respective pulleys connected by cables to the distal bending section, the motors being controlled by means of a joystick integrated in the control panel.

Videoendoscopes of recent design can also be associated with a digital system for freezing, processing, and storing images suitable for being controlled directly by the control panel of the videoendoscope.

In the architectures used by various present-day videoendoscope manufacturers:

- the video processor is integrated either in the control handle, or in the connection unit of the probe, or in the external unit containing the light generator;
- the video monitor may be integrated in the control handle or may be connected to the external unit; and
- the control panel of the video processor and of the video monitor may be integrated either in the control handle, or in the external unit.

The control handle of the videoendoscope constituting the subject matter of the present invention contains the video monitor, the control panel for the video processor, and possibly also the steering controls, the video processor being housed in a connection unit constituting the proximal end of the umbilical cable, or preferably being housed in the control handle.

Control handles of this type are usually in the form of an elongate unit secured to a video monitor disposed transversely on said unit. The inspection tube is secured to the distal end of the unit while the umbilical cable is secured to its proximal end. Generally, the control panel is integrated in the control unit.

As a result, the dimensions of the video monitor are necessarily small so as to avoid making the handle too heavy and unbalancing its center of gravity. It is therefore often necessary to connect the videoendoscope to an external video monitor of larger dimensions, thereby directly affecting the independence and the mobility of the equipment.

In addition, the user is hindered by the umbilical cable secured to the proximal end of the control handle.

One such control handle is described in U.S. Pat. No. 6,315,712 filed by the Applicant, and in U.S. Pat. No. 5,373,317.

U.S. Pat. No. 4,539,586 describes a connection module for a videoendoscope probe enabling the probe to be connected to an external unit that is specially adapted, including in particular a light generator, a video processor, and an electrical power supply. That connection module comprises electronic circuits such as amplifiers and clock delay compensators which are adjusted as a function of the length of the probe, so as to enable probes of different lengths to be connected thereto.

European patent application No. 0 587 514 also describes a connection module for a videoendoscope probe, the module including a video processor adjusted as a function of the length of the probe, said connection module being pluggable in a specific external unit housing a light generator and an electrical power supply.

The videoendoscopes described in those documents require the user to acquire a specifically-adapted external unit that includes a light generator and an electrical power supply presenting characteristics that are likewise specific. However, it often happens that the users of such videoendoscope probes already have light generators for such probes. In addition, it is preferable to be able to have a plurality of light generators available so as to be able to continue using a probe even in the event of one of the generators breaking down.

An example of an electromechanical device for controlling distal steering is described for example in U.S. Pat. No. 4,941,454. That electromechanical device comprises two servo-motors each actuating a respective pulley driving a pair of cables whose two ends are fixed to the distal bending section in order to transmit movements of the pulley thereto, thereby steering the articulated distal bending section in a plane, with the two planes in which the distal bending section is steered respectively by the two servo-motors being perpendicular to each other.

That device also includes a servo-motor control circuit generating a train of pulses for each servo-motor with the width of the pulses being adjusted by means of a potentiometer. The two potentiometers are actuated mechanically by the movements in two perpendicular planes of a joystick actuated manually by the user.

Because a joystick is used to actuate the potentiometers, prolonged manual action on the joystick leads to permanent deflection thereof and thus to a permanent specific steered configuration of the remote bending section. However as soon as the user releases the joystick, it returns to its neutral position, and the same applies to the bending section.

In addition, it is found that that solution does not enable the angular positions of the pulleys to be determined. That drawback is particularly troublesome, given that the user cannot perceive naturally the orientation of the bending section whose movements are controlled by the joystick.

In principle, when the joystick is in its middle position the bending section takes up a neutral orientation, i.e. it lies on the axis of the distal end of the probe. Consequently, if the joystick presents a permanent deflected position, the bending section likewise presents a permanent deflected orientation, which makes such a device awkward to use.

U.S. Pat. No. 5,658,238 describes another example of an electromechanical device for controlling a distal bending section, the device comprising direct current (DC) motors controlled by control buttons, the controlling electronics of that device being disposed in an external unit. That device requires encoders to be provided for determining the respective angular positions of the motors, and thus electronic servo-control of said angular positions.

Endoscopes and videoendoscopes presenting a flexible inspection tube are generally stored by winding the inspection tube around a drum.

U.S. Pat. No. 4,913,369 describes such a drum mounted to turn on a base and comprising a foam hub presenting housings for storing the distal endpiece of the probe and the connector situated at the proximal end, said housings being closed by a side cover. As a result such a drum must be removed from its storage case before it is possible to use the probe.

European patent No. 0 276 139 and U.S. application Ser. No. 2002/0 032 365 describe storage drums for videoendoscope probes, with the probes being wound around said drums beginning by the distal end, the hub of a drum including means for connecting the proximal end of the probe to an electrical power supply and a light source. That enables the probe to be used without it being necessary to unwind it completely from the drum. Nevertheless, that solution presents the drawback of requiring the light source and the video processor to be integrated in the hub of the drum and rotary electrical connectors to be provided for powering the probe, where such connection means are very expensive, not very reliable in the long term, and give rise to electrical losses. In addition, that solution makes the probe unusable with a different storage case.

Furthermore, U.S. Pat. No. 5,314,070 describes a storage case for a videoendoscope or endoscope inspection tube comprising a spiral-wound storage tube in which the inspection tube is engaged. As a result, on each insertion and extraction into and from the storage case, the inspection tube and in particular its distal endpiece rubs against the inside wall of the storage tube. Once a certain length of the inspection tube has been engaged in the storage tube, the force needed to overcome friction forces becomes very large and there is a danger of damaging the inspection tube, and in particular the junction between the inspection tube and the control handle, by exaggerated twisting of the inspection tube. This risk of twisting requires the sheath of the inspection tube to be reinforced, at least in the vicinity of the control unit, thus leading to extra cost. Furthermore, that solution is not suitable for endoscopes having an inspection tube that is long, in particular longer than 6 meters (m).

OBJECTS AND SUMMARY OF THE INVENTION

An object of the present invention is to make such a videoendoscope more ergonomic. This object is achieved by providing a videoendoscope comprising:

an inspection probe comprising an inspection tube having a distal endpiece housing an optoelectronic imaging device delivering an electrical signal;

a video processor for processing the electrical signal delivered by the imaging device in order to generate a video signal;

a control handle comprising a control unit secured to the proximal end of the inspection tube and provided with means for controlling and adjusting the video processor;

an umbilical connection cable whose distal end is secured to the control unit for connecting the videoendoscope to a light source and to an electrical power supply;

a display unit including a video display screen connected to the video processor in order to display the video signal; and a bundle of lighting fibers integrated without interruption in the umbilical cable, in the control handle, and then in the inspection tube, and having a distal end housed in the distal endpiece that serves to light a target observed by the probe when the proximal end of the umbilical cable is connected to a light generator.

According to the invention, the display unit is secured to a side face of the control unit, the control unit having a control panel on a top face and carrying the means for controlling and adjusting the video processor, and being of elongate shape between its distal end and its proximal end so as to be suitable for being held in one hand while allowing the control members to be actuated by using the thumb of said hand.

Advantageously, the umbilical cable is connected to the control unit via a side face thereof.

In an embodiment of the invention, the display unit is secured to the control unit via a hinge enabling the display screen to be tilted about an axis perpendicular to the side face of the control unit, the display unit being electrically coupled to the control unit by means of electrical conductors passing through the hinge.

Advantageously, the hinge is constituted by a connector providing releasable mechanical and electrical connection between the display unit and the control unit.

In an embodiment of the invention, the proximal end of the umbilical cable is secured to a connection unit fitted with connection means for connection to the proximal end of the bundle of lighting fibers and to a light generator, and connection means for connecting the videoendoscope probe to an electrical power supply.

Advantageously, the connection endpiece has fixing means for fixing a mechanical adapter to adapt the connection endpiece to the connection endpiece of any light generator, the control panel including a control member for controlling initialization of the video processor as a function of the color temperature of the lamp of the light generator.

Preferably, the video processor is included in the control unit.

In an embodiment of the invention, the control unit has mechanical and electrical coupling means on both side faces to enable the display unit to be fixed and electrically connected to either side face of the control unit.

Alternatively, the video processor is integrated in the display unit or in a connection unit for connecting the proximal end of the umbilical cable to an external unit.

Another object of the present invention is to provide the user with the possibility of connecting a videoendoscope probe having its own video processor to a light generator of the user's choice, to a standard electrical power supply, and/or to an external unit including, in particular, a system for processing and storing video images.

This object is achieved by the fact that the connection unit further comprises connection means for connecting the probe to a system for processing and/or storing images, the videoendoscope probe further comprising switch means designed to deliver to the video screen either the video signal coming from the video processor or the video signal coming from the system for processing and/or storing images.

Advantageously, the control unit has means for controlling a system for processing and/or storing images, which system is connected to the connection means of the connect unit, said connection means including a pin for transmitting the video signal generated by the video processor to a video input of the system for processing and/or storing images, a pin for transmitting to the switch means a video signal generated by the system for processing and/or storing images, and a pin for connecting the control means of the control unit to a control interface of the system for processing and/or storing images.

Preferably, the videoendoscope further comprises means for controlling the switch means to direct the video signal coming from the system for processing and/or storing images to the video screen immediately said system is connected to the connection means.

In an embodiment of the invention, the switch means are integrated in the control unit, or in the display unit or in the connection unit.

In an embodiment of the invention, the connection means for connecting the probe to a system for processing and/or storing images includes a connection pin enabling the videoendoscope to be powered from an electrical power supply associated with the system for processing and/or storing images.

In an embodiment of the invention, the connection unit includes means for connecting the videoendoscope probe to an auxiliary electrical power supply.

In an embodiment of the invention, the connection unit includes means for connecting the videoendoscope probe to an auxiliary video monitor, the switch means including means for sending the video signal applied to the input of the video screen towards the connection means for connection to the auxiliary video monitor.

Advantageously, the control handle has means for controlling the switch means.

Another object of the present invention is to fit such a videoendoscope with a distal bending section enabling the distal endpiece of the probe to be steered in order to change its field of view while avoiding the above-described drawbacks of prior art solutions. This object is achieved by the fact that the control unit further includes:

an electromechanical device designed to deform a deformable distal bending section integrated in the distal end of the inspection tube in order to steer the distal end of the inspection tube and thus steer the observation window of the probe, the electromechanical device comprising two motors actuating the distal bending section via two respective pairs of cables for steering the distal end of the inspection tube in two respective planes;

a processor delivering two control signals that are applied respectively to the two motors; and command input means comprising two command input members connected to the processor to input commands intended for the two motors respectively, each of the two command members having a first state in which the processor controls the corresponding motor to keep the orientation of the distal end of the inspection tube fixed, and second and third states in which the processor controls the respective motor to cause the distal end of the inspection tube to vary its orientation respectively in one direction and in the opposite direction.

Advantageously, each of the motors is of the servo-motor type actuating a pulley coupled to a respective cable pair and of angular position that can be controlled by the respective control signal generated by the processor and applied to the motor, each control signal being in the form of a pulse train, with the width of the pulses corresponding to a determined angular position of the pulley, the processor comprising means for keeping the width of the pulses in each control signal constant so long as the respective control member is in its first state, and for increasing and decreasing the width of the pulses at a predefined speed whenever the corresponding control member is respectively in its second or third state.

Preferably, it includes an additional control member integrated in the control panel and connected to the processor to cause the width of the pulses in the control signals applied to the motors to be controlled in such a manner as to be equal to a middle value corresponding to zero deformation of the distal bending section.

Advantageously, the additional control member is integrated in the control input means for controlling the distal bending section.

In an embodiment of the invention, each of the two control members comprises a pair of contacts which are both open in the first state, with one or other of the contacts being closed in the second and third states.

In an embodiment of the invention, each of the control members comprises two pushbuttons integrated in the control panel to actuate two respective contacts which are in the open state when at rest, and which pass to the closed state when the corresponding pushbutton is held pressed down.

In an embodiment of the invention, the means for inputting commands for the bending section comprise a joystick suitable for actuating both command input members simultaneously.

Preferably, the videoendoscope includes an additional control member integrated in the control panel to modify the speed at which the distal end of the inspection tube is steered by selecting a slow speed or a fast speed.

Alternatively, the processor is programmed to select a fast speed of variation for steering the distal end the inspection tube if at least one of the two control members is maintained in the second or third state for a duration longer than a predefined threshold, and to select a slow speed for varying the steering of the distal end of the inspection tube if both control members are in the first state.

Advantageously, the processor is programmed to determine the orientation of the distal end of the inspection tube as a function of the form of the control signals applied respectively to two motors, and to display on the display screen symbols representing the determined orientation.

Another object of the present invention is also to provide a storage case for such a videoendoscope that avoids the above-described drawbacks of the prior art.

This object is achieved by the fact that the videoendoscope includes a storage and transport case containing an electrical power supply and a lighting generator, the storage case containing a drum around which the probe can be wound, the drum being mounted in such a manner as to be capable of turning freely about its axis and having a tubular cavity for receiving the distal end of the probe, and opening out tangentially to the cylindrical surface of the drum.

Advantageously, the drum comprises a central hub held between two side plates on the same axis, the cavity being made from one of the side faces of the hub and being closed latterly by one of the two side plates.

Preferably, the central hub is made of a material presenting a high coefficient of friction.

Also preferably, the central hub is made of a hard cellular foam.

In an embodiment of the invention, the storage case has a housing in which the drum is secured, the housing possessing an opening giving access to a portion of the cylindrical surface of the drum.

In an embodiment of the invention, the case has a lid whose inside face is covered in foam, the drum being mounted in the case in such a manner as to be prevented from rotating by the foam in the lid when the lid is closed on the case.

Preferably, the inside diameter of the cylindrical cavity is slightly greater than the greatest diameter of the distal end of the probe that is to be wound about the drum.

BRIEF DESCRIPTION OF THE DRAWINGS

A preferred embodiment of the invention is described below by way of non-limiting example and with reference to the accompanying drawings, in which.

MORE DETAILED DESCRIPTION

Figure 1:
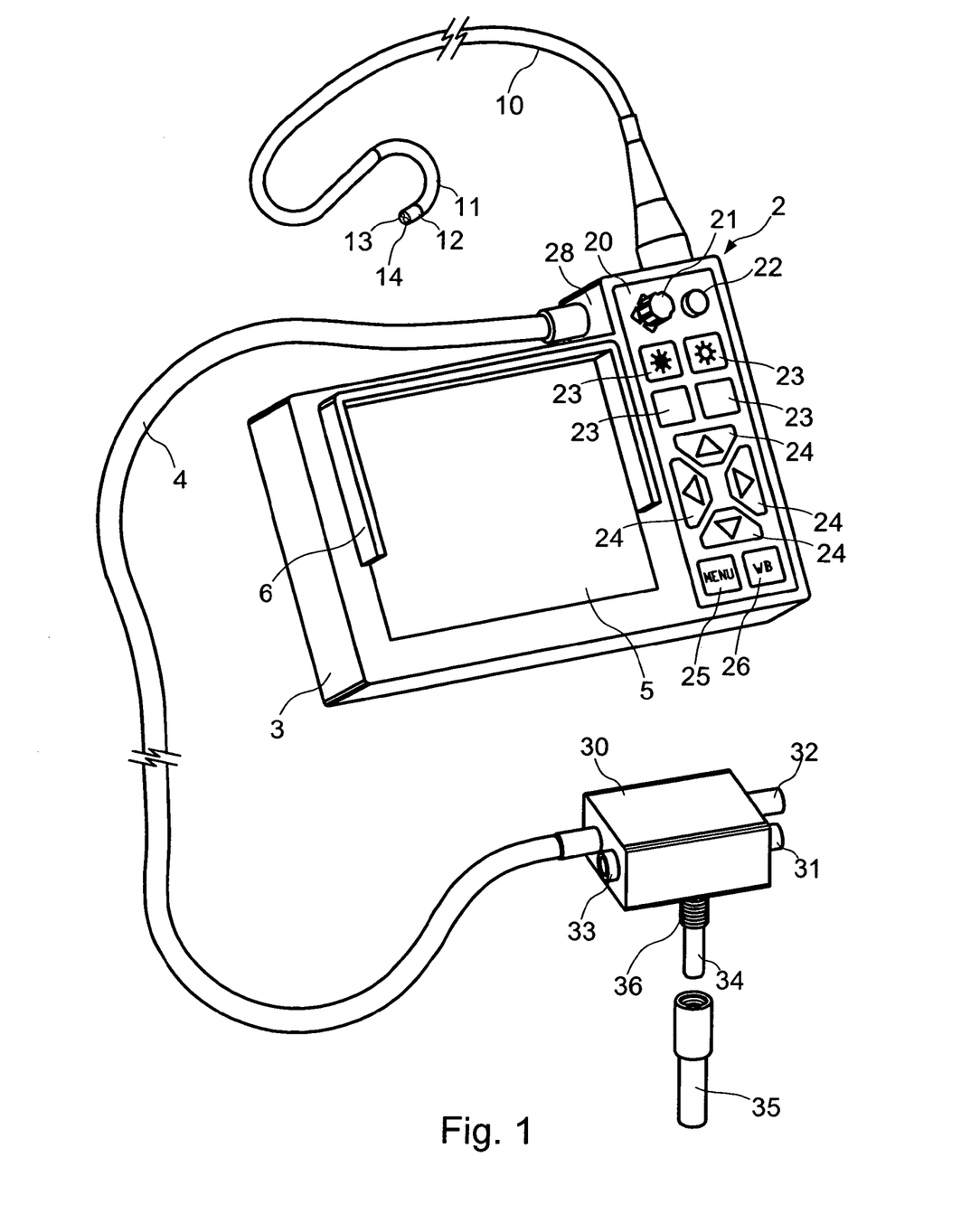
FIG. 1 is a diagrammatic perspective view of a videoendoscope fitted with a control handle in accordance with the invention.
Figure 2:
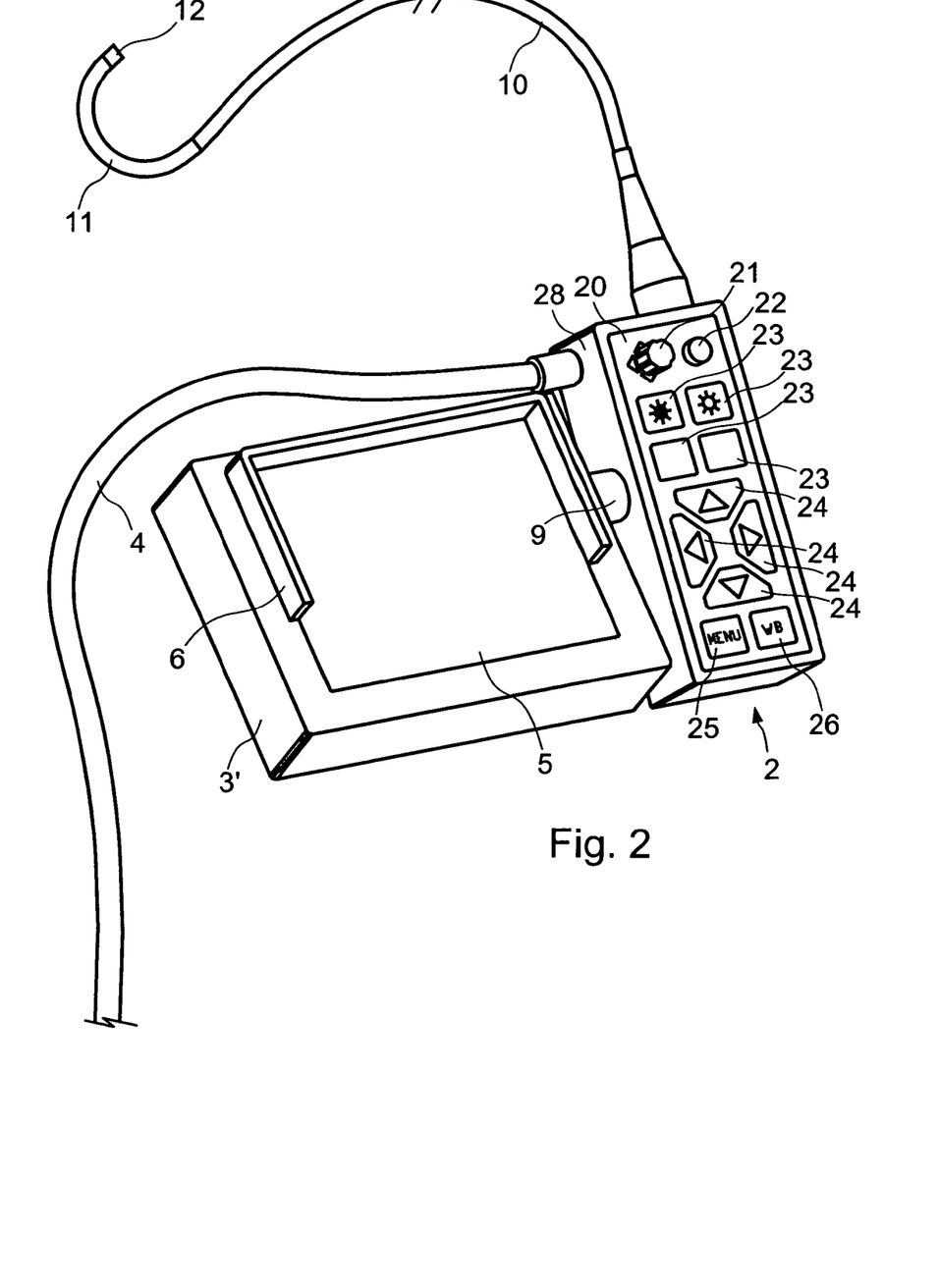
FIG. 2 is a diagrammatic and fragmentary perspective view showing a variant in accordance with the invention of the control handle shown in FIG. 1.

FIGS. 1 and 2 show a videoendoscope comprising a control handle made up of a control unit 2 substantially in the form of an elongate rectangular parallelepiped presenting a distal end to which the proximal end of a videoendoscope inspection probe is connected.

Figure 3:
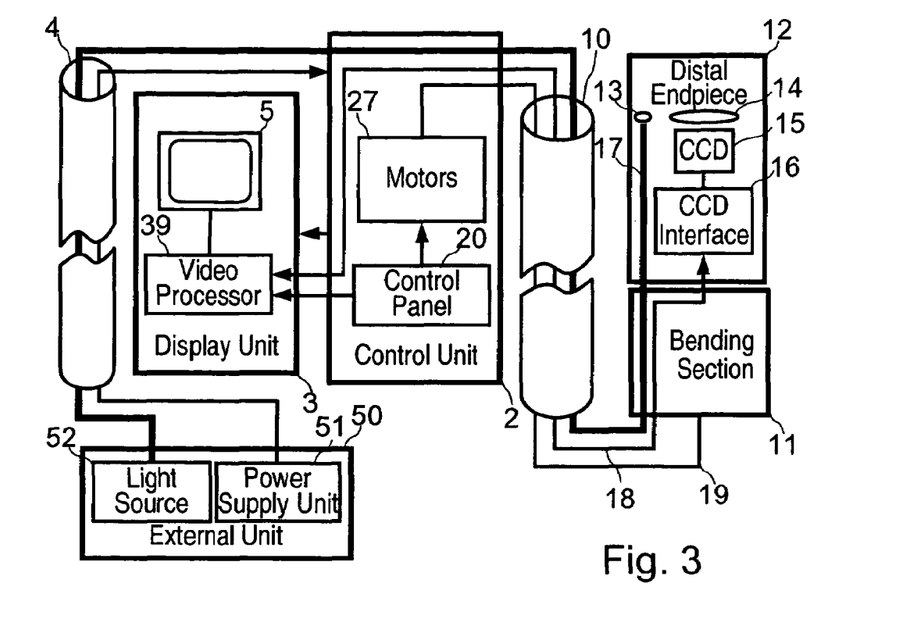
FIG. 3 is a block diagram showing the internal architecture of the videoendoscope shown in FIG. 1.

The control unit 2 is also coupled to an umbilical cable 4 whose proximal end is secured to a connection device 40 enabling the endoscope probe to be connected to a light source 52 and to an electrical power supply 51 (see FIG. 3).

The inspection probe comprises an inspection tube 10 and a distal endpiece 12 connected to the distal end of the inspection tube. The distal endpiece 12 conventionally contains an imaging device comprising a distal objective lens 14 forming a real image of the observed target on the photo-sensitive layer of a CCD sensor 15 (see FIG. 3), preferably a color sensor, with which the objective lens is associated. The CCD sensor is coupled to an interface microcircuit 16 for correcting the electrical signals received or generated by the CCD sensor. The interface circuit 16 is connected to the control handle 2 by a multiconductor cable 18 that passes along the inspection tube 10 and that conveys voltages for powering the imaging device, signals for synchronizing the CCD sensor, and the electrical signal delivered by said sensor.

The control handle also comprises a display unit 3 secured to the control unit 2 and containing a video processor 39 connected to the imaging device by the multiconductor link cable 18 that passes along the inspection tube 10, and a display screen 5, e.g. of the video monitor type, possibly a color monitor, controlled by the video processor and housed in the display unit. The display screen 5 is preferably flat and lightweight, e.g. being of the liquid crystal display (LCD) type, and the display unit 3 presents dimensions that correspond substantially to those of the display screen.

Provision can be made for the top edge and a top portion of the side edges of the display screen 5 to be raised so as to form a sunshield 6.

The control unit 2 has a top face on which a control panel 20 is disposed comprising buttons 23 to 26 for controlling the endoscope and the video monitor 5.

More precisely, the control panel 20 has the following buttons:
- a set of buttons 23 for directly adjusting the main parameters of the video processor 39 and the video monitor 5 (in particular brightness and contrast);
- a button 25 giving access to a menu for selecting functions for adjusting all of the operating parameters of the video processor;
- four directional or navigation buttons 24 for selecting options in the various menus accessed by means of the button 25; and
- a button 26 for controlling white balance which is applied to the video processor.

The distal face of the endpiece 12 also has a lighting window 13 in register with the distal end of a continuous bundle of lighting fibers 17 housed in the inspection probe 10, in the control handle 2, and then in the umbilical cable 4 so as to connect the lighting window 13 without any interruption to the proximal end of the umbilical cable 4 secured to a lighting connection endpiece 34 housed in the connection unit 30 of the videoendoscope probe. The lighting window 13 is disposed on the distal endpiece 12 in such a manner as to light the target situated in the field of view of the optical window 14 when the lighting endpiece 34 of the connection device 30 is connected to a light generator 52 (see FIG. 3).

Furthermore, the inspection probe may include an articulated distal bending section 11 which is deformed under the control of cables 19 housed in the inspection tube 10 and actuated by a control card 27 including motors and housed in the control unit 2 (see FIG. 3). In this case, the control unit 2 includes a control device 21 having four degrees of freedom, e.g. of the joystick type, connected to the control card in order to control the motors.

In a first preferred variant of the invention, the display unit 3 is secured to a side face 28 of the control unit 2.

In this way, the user can hold the assembly comprising the control unit 2 and the display unit 3 in both hands, one hand holding the control unit and the other the display unit. Because of the elongate shape of the control unit 2, the user can simultaneously hold the control unit and display unit assembly and can also access all of the buttons on the control panel 20 using the thumb.

In addition, the dimensions of the display screen 5 may be considerably larger than is possible with control handles of the prior art.

By means of the invention, there is thus no need to make use on all occasions of an external video monitor, thus improving the advantages of the videoendoscope in terms of ability to operate independently, mobility, and simplicity and ease of implementation and use.

The umbilical cable 4 is preferably connected to the control unit 2 via a side face thereof. In this way, the user is less impeded by the cable. Naturally, the zone where the umbilical cable 4 is connected to the control unit 2 can be the side face 28 to which the display unit 3 is connected or the other side face of the control unit 2.

The side face 28 is preferably situated on the left-hand side for the user, thus enabling the user to actuate the control panel 20 of the control unit 2 using the right hand.

In another preferred variant of the invention, as shown in FIG. 2, the display unit 3' is secured to the control unit 2 via a hinge 9 enabling the screen 5 to be tilted relative to the control unit 2 about an axis perpendicular to its side face 28. This disposition enables the screen 5 to be tilted as a function of its position relative to the eyes of the user, and to eliminate reflections. In this case, the wires providing electrical connections between the display unit and the control unit advantageously pass via the hinge 9.

In the two variants of the invention described above, provision can be made for the display unit 3, 3' to be removable and disconnectable from the control unit 2. In which case, the display unit is pluggable sideways onto the control unit 2.

In the second variant, the hinge 9 may be constituted by a connector providing both electrical connection and mechanical connection for the display unit 3' on the side of the control unit 2, while still allowing these two units to pivot relative to each other and to be separated.

In both variants, the control unit 2 may have mechanical and electrical coupling means on two side faces so as to enable the display unit 3, 3' to be secured and connected electrically to either side face of the control unit, depending on whether the user is right-handed or left-handed.

Figure 4:
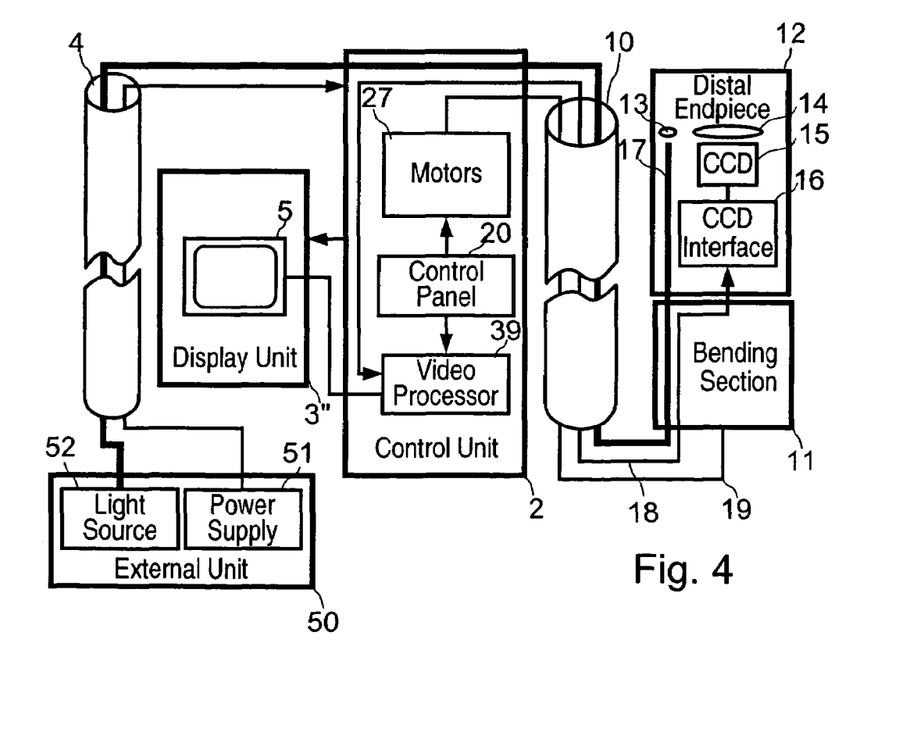
FIG. 4 is a block diagram showing the internal architecture of an endoscope constituting a variant of the architecture shown in FIG. 3.

In another variant of the invention as shown in FIG. 4, the video processor is housed in the control unit 2. In this way, the control unit 2 of the invention can be used either with a display unit 3" with which it is electrically and mechanically coupled in releasable manner, or else with an external video monitor via a connection cable.

It should be observed that because the video processor is located in the control handle, the multiconductor electrical cable connecting the video processor to the CCD interface circuit 16 is of fixed length. As a result the video processor can be set in the factory as a function of the length of the cable.

Figure 5:
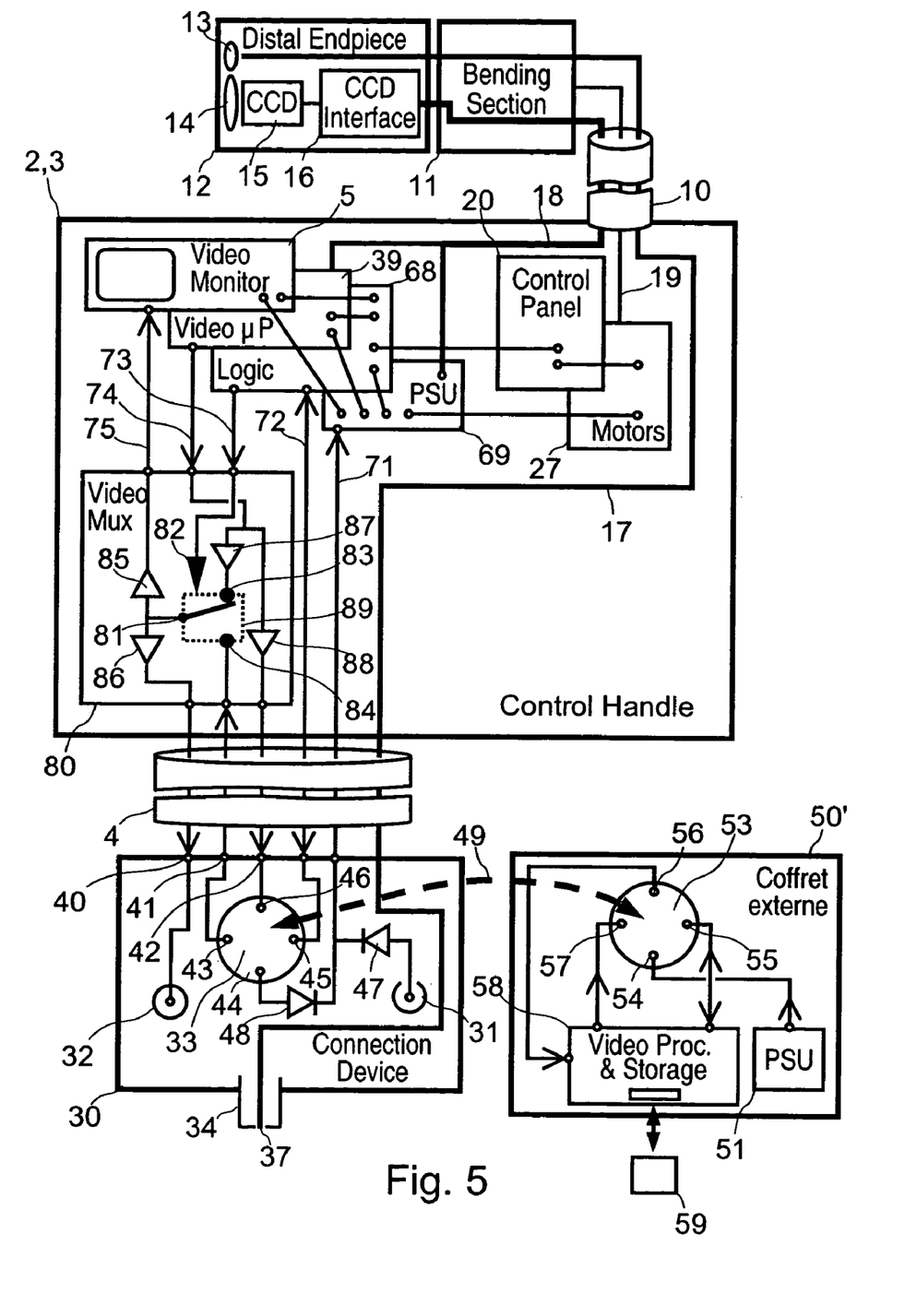
FIG. 5 is a block diagram showing in greater detail a variant of the internal architecture of the videoendoscope shown in FIG. 1.

As shown in FIG. 5, the control handle 2 also houses a video multiplexer 80 enabling the video screen 5 to display either the image delivered by the video processor, or else video images delivered by a device 58 for processing and/or storing images and suitable for being connected to the connection device 30 via a connection cable 49.

The umbilical cable 4 houses both a bundle of lighting fibers 17 for the videoendoscope probe and also a multiconductor electrical cable along which a general electrical power supply voltage is conveyed to the control handle 2, together with a video signal delivered by the video multiplexer 80, logic control signals interchanged between the control handle 2 and a device 58 for processing and/or storing video images and suitable for connection to the connection device 30, and a video signal delivered by the device for processing and/or storing images.

The connection device 30 is fitted with a cylindrical connection endpiece 34 connected to the proximal end of the bundle of fibers for lighting the videoendoscope probe. The connection endpiece 34 has a thread 36 for receiving a mechanical adapter 35 corresponding to the mechanical standard of the lighting connector of a light generator 52 as selected by the user. The connection device 30 also comprises a connector base 31 suitable for being connected to a DC power supply, a video output connector base 32 receiving the video signal output by the video multiplexer housed in the control handle 2 and suitable for connection to an auxiliary video monitor, and a multipin connector base 33 for connection to an external device 58 for processing and/or storing video images.

The touch-sensitive buttons 23, 24, and 25 of the control panel 20 enable the user both to manage the video functions of the video processor housed in the control handle 2, and the functions of the device 58 for storing and/or processing images and suitable for being connected to the multipin connector base 33 of the connection device 30. The touch-sensitive button 26 serves to adjust automatically the white balance of the video processor 39 as a function of the spectral characteristics of the lighting delivered by the lighting window 13 of the distal endpiece 12 of the inspection tube 10, and thus the spectral characteristics of the lamp in the light generator to which the lighting connector 34 of the connection device 30 is connected.

More precisely, in FIG. 5, the control handle 2 houses the following elements:

the electromechanical assembly 27 combining two servo-motors for actuating cables 19 for controlling the bending section 11 situated at the distal end of the inspection tube 10, together with electronic devices for managing said servo-motors;

the video processor 39 connected to the distal CCD sensor 15 of the videoendoscope probe by a multiconductor cable 18 housed in the inspection tube 10 and along which there pass synchronization signals for the CCD sensor as generated by the video processor, the electrical signal generated by the CCD sensor, and the electrical power supply for the CCD sensor, the video processor delivering a standard video signal over a link 74 which is connected to an input of the video multiplexer 80;

the video screen 5 connected via a link 75 to an output of the multiplexer 80 and enabling the video signal delivered by the video multiplexer to be viewed;

a logic card 68 generating over a link 73 a control signal for the video multiplexer 80 and control signals for the video processor 39 and the video screen 5, and over a link 72 control signals for the external device 58 for processing and storing images, as a function of commands input by means of the control panel 20;

the control panel 20 with its buttons generating orders both for the devices that manage the servo-motors that control the bending section, and also for the logic card 68; and a power supply circuit 69 receiving over a link 71 an external power supply voltage and generating the power supplies needed by the various elements 5, 27, 39, and 68 of the control handle 2, and also the power supply voltages needed by the imaging device integrated in the distal endpiece 12 of the inspection tube 10.

The video multiplexer 80 includes a switch 89 having two inputs 83 and 84, an output 81, and a control input 82. A first input 83 of the switch 89 receives, via an amplifier 87, the video signal 74 delivered by the video processor 39. The second input 84 of the switch 89 receives the video signal delivered by the external device for processing and storing images. The output 81 of the switch 89 delivers the video signal selected by the switch 89 to the video screen 5 via an amplifier 85, and via an amplifier 86 and a coaxial connection 40 to the connector base of the video output 32 from the connection unit 30. The control input 82 of the switch receives via the link 73 the logic signal delivered by the logic card 68.

The connection device 30 houses the proximal end 37 of the bundle of lighting fibers 17 of the videoendoscope probe.

The connector base 31 for connection to an auxiliary power supply is connected via a diode 47 and the cable 71 to the power supply card 69 housed in the control handle.

The connector base 33 has four pins 43, 44, 45, and 46 which may be connected, as shown in FIG. 5, by means of a cable 49 to a connector base 53 having four pins 54, 55, 56, and 57 provided on an external unit 50'.

The power supply pin 44 is connected via a diode 48 and the cable 71 to the power supply card 69 housed in the control handle. The pin 45 is connected via the link 72 to the logic card 68 included in the control handle 2 in order to allow control signals issued by the logic card 68 in the control handle 2 to travel to the external device 58 for processing video images. The pin 46 receives via a link 42 and an amplifier of the video multiplexer 80 the video signal 74 delivered by the video processor 39 housed in the control handle 2. The pin 43 delivers the video signal generated by the image processing device 58 over the link 41 connected to the input 84 of the video switch 89.

Advantageously, the connector base 39 has an additional pin (not shown) which is connected to the logic card 68 in order to trigger activation of the multiplexer 80 as soon as an image processor system is connected to the connector base 33.

Naturally, the video multiplexer 80 may alternatively be integrated in the display unit 3 or in the connection unit 30. In which case, the video processor 39 may also be integrated in the connection unit.

The above-described videoendoscope probe fitted with the multiplexer 80 and the connection device 30 can be connected to any light generator by using an adapter 35 corresponding to the connector base of the generator. It may also be connected to an auxiliary video monitor and to a system 58 for processing and/or storing images, while still making it possible to view the images recorded by such a system on the screen of the control handle, and to control the system from the control handle. Thus, the four navigation buttons 24 (arrows pointing in four directions) on the control handle can be configured for acting in normal operation to cause the image viewed on the screen 5 to be recorded (up arrow), the most recently recorded image to be deleted (down arrow), the previous recorded image to be displayed on the screen 5 (left arrow), and the next image to be displayed on the screen (right arrow).

These dispositions make the endoscope probe of the invention very flexible and ergonomic in use.

Figure 6:
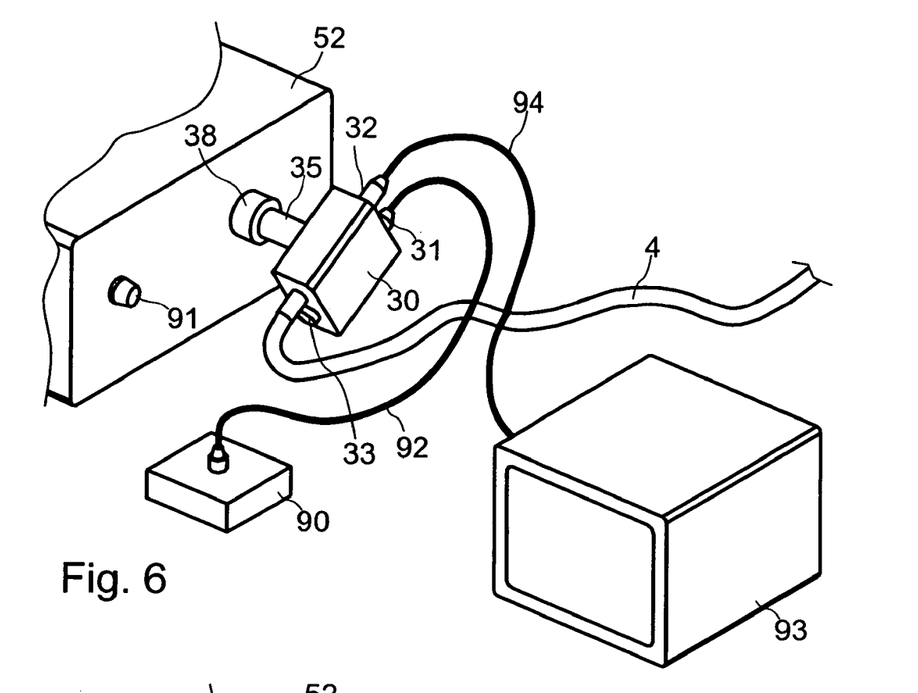
FIG. 6 is a diagram showing the architecture of a simplified video system associating the videoendoscope probe shown in FIG. 1 with a light generator and an electrical power supply.

As shown in FIG. 6, the videoendoscope of the invention may be integrated in a simple video system comprising a light generator 52 and a conventional DC power supply 90.

For this purpose, the adapter 35 is screwed onto the lighting connection endpiece 34 of the connection display 30 and is plugged into a lighting connector 38 of the light generator 52 and the amount of light delivered can be controlled by turning a knob 91 for controlling a diaphragm. In addition, the electrical power supply connector 31 of the connection device 30 is connected by a cord 92 to the external power supply 90.

The video output connector base 32 of the connection device 30 can be connected via a coaxial cord 94 to an auxiliary video monitor 93 enabling the video signal generated by the video processor integrated in the control handle of the videoendoscope probe to be viewed, in which case the image on the auxiliary monitor 93 is identical to the image displayed on the video screen 5 of the control handle.

Figure 7:
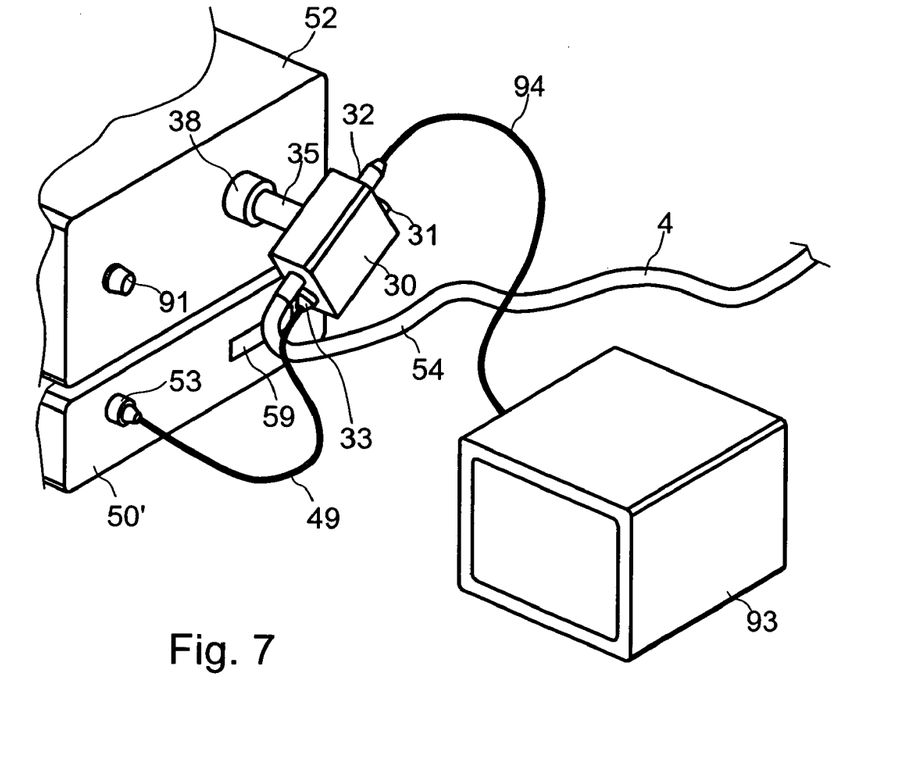
FIG. 7 is a diagram showing the architecture of a complex video system associating the videoendoscope probe shown in FIG. 1 with a light generator and an external power supply unit containing a specific device for processing and storing video images.

As shown in FIG. 7, the videoendoscope probe of the invention can be integrated in a video system that is more complex, comprising a light generator 52 and an external unit 50' containing, as shown in greater detail in FIG. 5, a DC power supply 51 and a device 58 for processing and/or storing video images on a memory card 59 that is preferably removable.

To this end, the adapter 35 screwed onto the lighting connection endpiece 34 of the connection device 30 is plugged into the lighting connector 38 of the light generator 52 and the amount of light delivered can be controlled by turning the diaphragm control knob 91.

The multipin connector base 33 of the connection device 30 is connected via the multiconductor cord 49 to the multipin connector base 53 of the external unit 50'.

In the external unit 50' shown in greater detail in FIG. 5 the pin 54 of the multipin connector 53 for connection to the pin 44 of the connector base 33 is connected to the power supply circuit 51. The pin 56 for connection to the pin 46 is connected to a video input of the device 58 for processing and storing video images. The pin 57 for connection to the pin 43 is connected to a video output of the device 58. The pin 55 for connection to the pin 45 is connected to a logic control input/output of the dialog device 58.

The cord 49 conveys the following signals:
the video signal generated by the video processor integrated in the control handle 2.
the video signal generated by the device 58 for processing and/or storing images that is included in the external unit 50';
the power supply voltage generated by the external unit 50'; and
the control signals for the unit 50' as generated by the control handle as the result of the user activating the buttons 24 of the control panel 20.

As for the system shown in FIG. 6, an auxiliary video monitor 93 may be connected via a coaxial cord 94 to the video output connector base 32 of the connection device 30 in order to use said auxiliary monitor to view the video images delivered by the video multiplexer included in the control handle, these images being identical to those displayed on the video screen 5 of the control handle.

Figure 8:
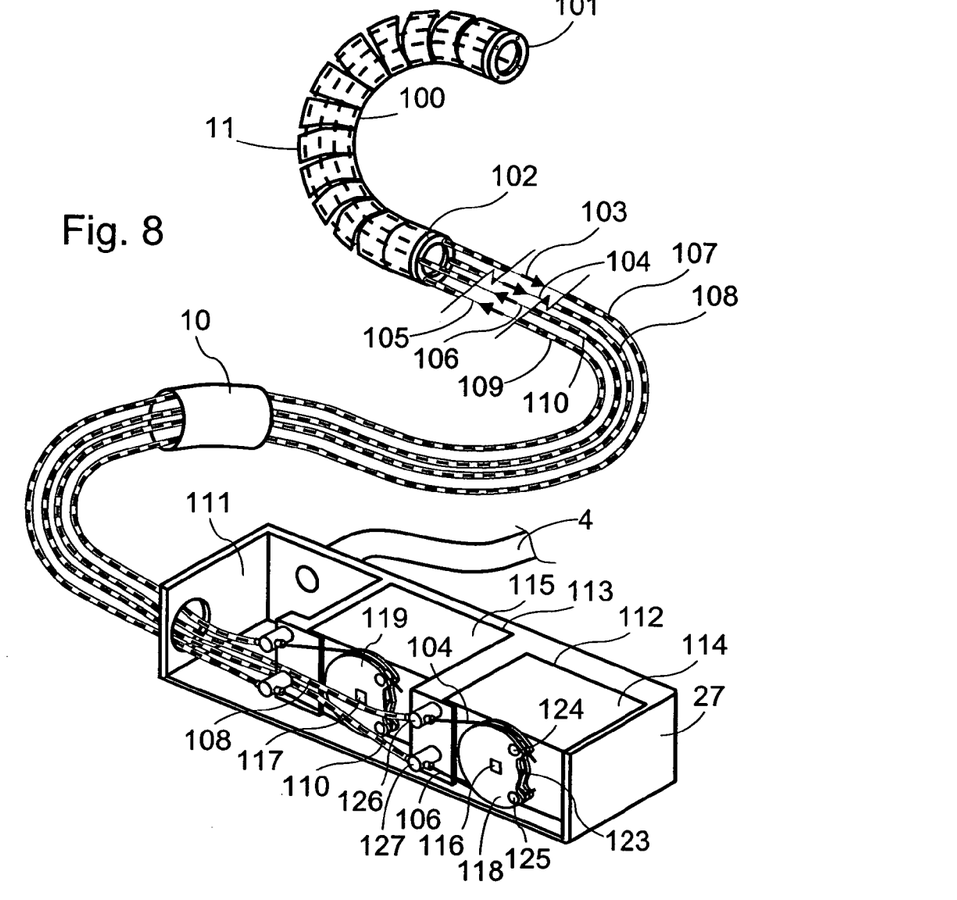
FIG. 8 shows an electromechanical device for actuating a distal bending section suitable for being fitted to the videoendoscope probe shown in FIG. 1.

As shown in FIG. 8, the distal bending section 11 is steered in two perpendicular planes under the control of two pairs of drive cables 103 & 105 and 104 & 106 housed in the inspection tube 10 and actuated by an electromechanical device 27 housed in the control handle 2.

This device comprises two servo-motors 114, 115 and a servo-motor control device. The two servo-motors 114, 115 turn respective pulleys 118, 119 via respective shafts 116, 117, the pulleys actuating two respective pairs of cables 103 & 105 and 104 & 106, the distal ends of both pairs of cables being fixed to the bending section 11 in order to control steering thereof in two respective mutually-perpendicular planes.

The servo-motors 114, 115 and the servo-motor control device are housed in the control handle 2 which, for this purpose, has three compartments 111, 112, and 113. The compartment 111 secured to the proximal end of the inspection tube 10 houses the control circuit for the servo-motors 114 and 115, while the other two compartments 112 and 113 house the servo-motors 114 and 115 respectively.

The compartments 112 and 113 are advantageously offset transversely so that their pulleys 118 and 119 are suitably positioned in two parallel planes.

The distal bending section 11 of the inspection probe 10 is constituted by a series of rings 100 connected to one another by hinges enabling said bending unit to be deformed so as to steer its distal end in two perpendicular planes. The last ring constituting the distal end of the bending section 2 is secured to a ring 101 that is pierced by four longitudinal holes disposed at 90° to one another and having the distal ends of the four drive cables 103, 104, 105, and 106 fixed therein. The last ring constituting the proximal end of the bending section 11 is likewise securely fixed to a ring 102 pierced by four longitudinal holes disposed at 90° to one another and in which the four cables 103 to 106 can slide freely. The proximal face of said ring also serves as a stationary abutment for four flexible sheaths 107, 108, 109, and 110 in which the four cables 103 to 106 slide respectively.

Figure 9:
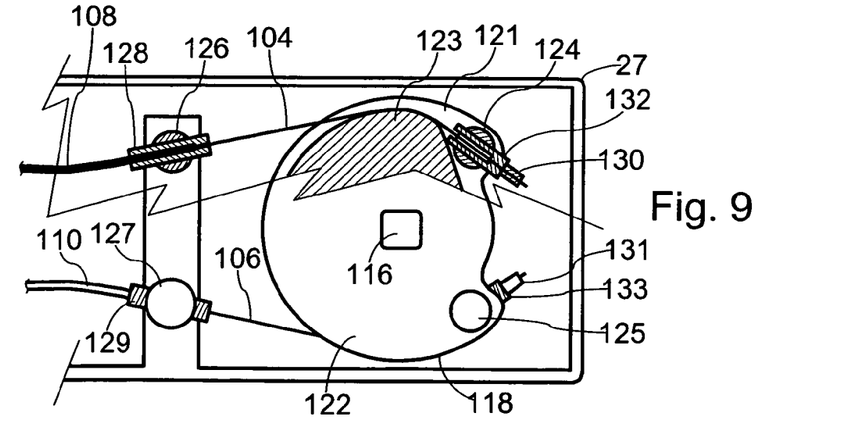
FIG. 9 shows a portion of the electromechanical device shown in FIG. 8 in greater detail.
Figure 10:
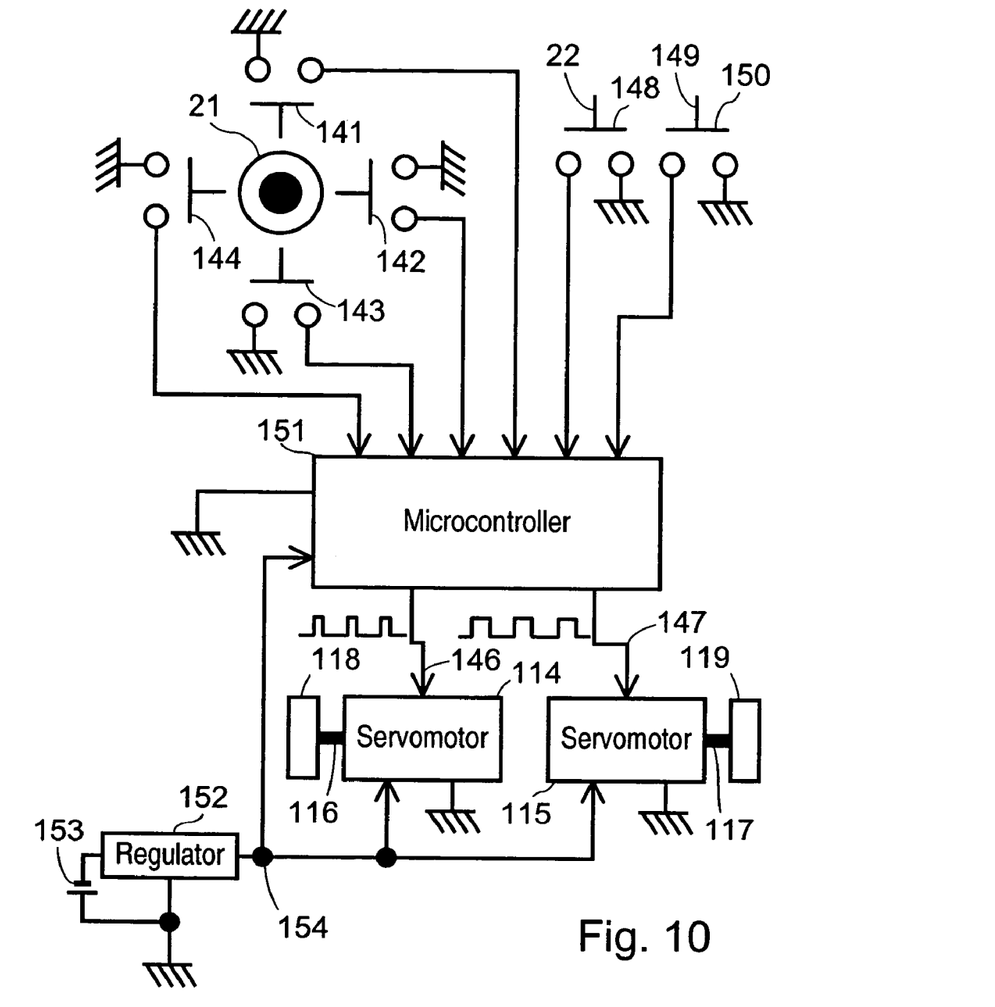
FIG. 10 shows an electronic control circuit of the invention for the electromechanical device shown in FIGS. 8 and 9.
Figure 11:
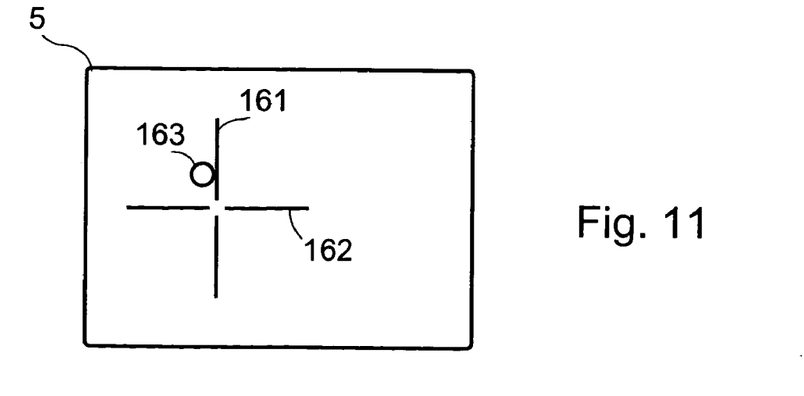
FIG. 11 shows a way of representing the orientation of the distal bending section on a video screen.
Figure 12:
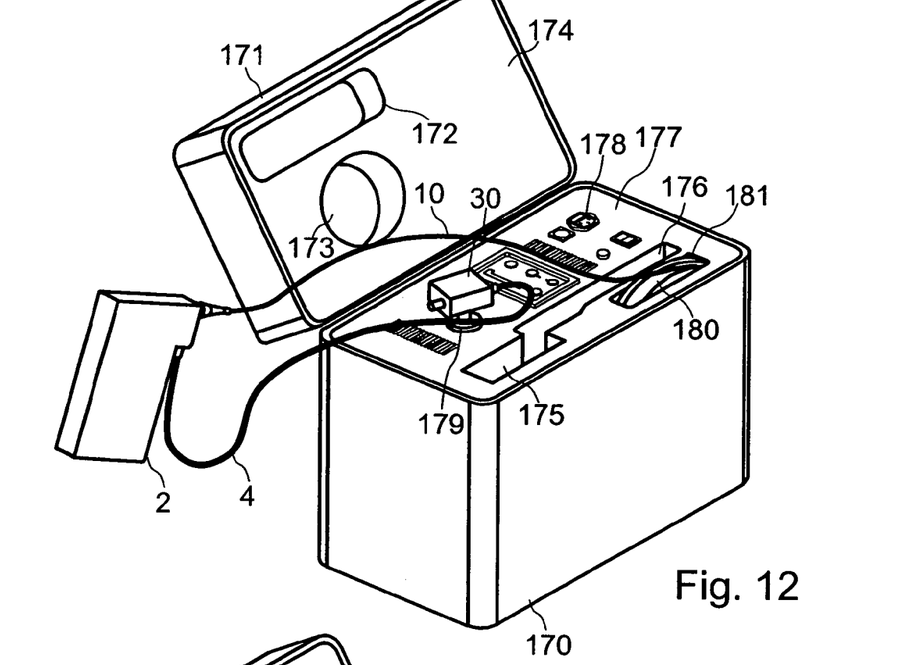
FIG. 12 is a diagrammatic perspective view of a case for storing and transporting a videoendoscope probe of the invention, the probe being shown outside the case.
Figure 13:
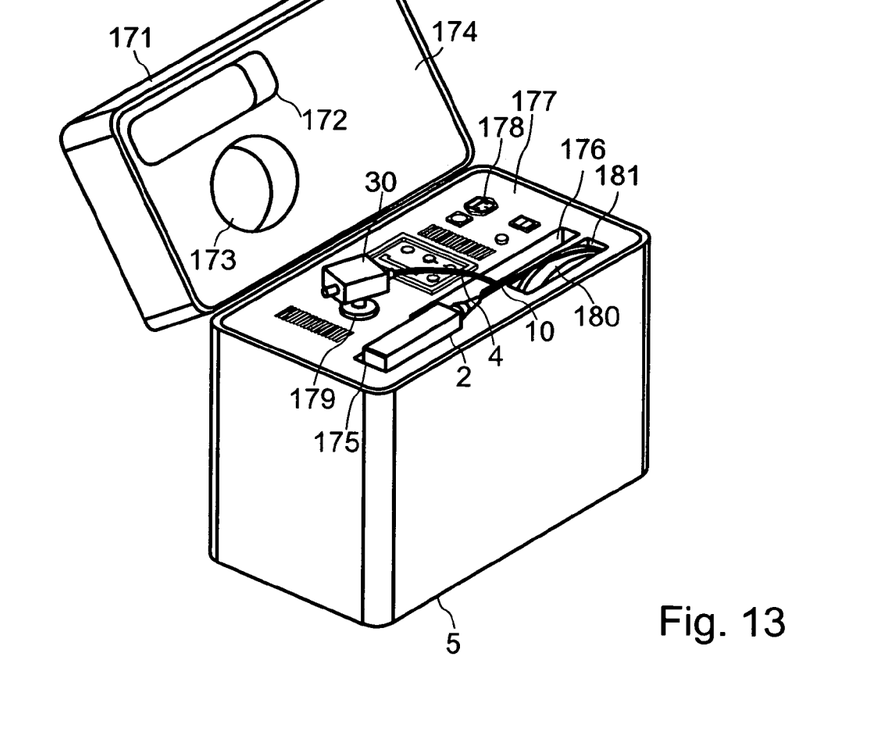
FIG. 13 is a diagrammatic perspective view of the storage and transport case shown in FIG. 12 with the probe in place in the case.
Figure 14:
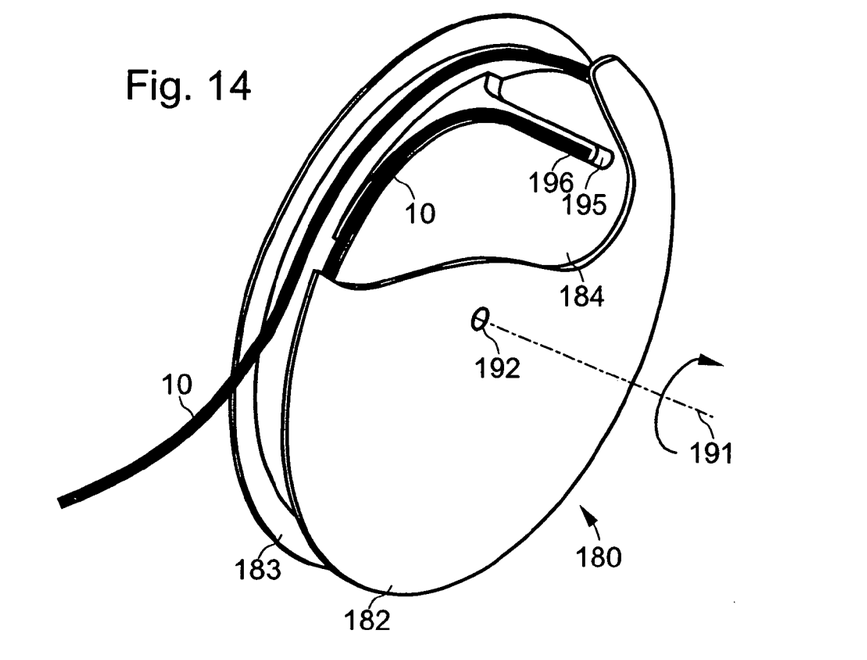
FIG. 14 is a partially exploded perspective view showing a detail of the drum on which an endoscope inspection tube of the invention is wound.
Figure 15:
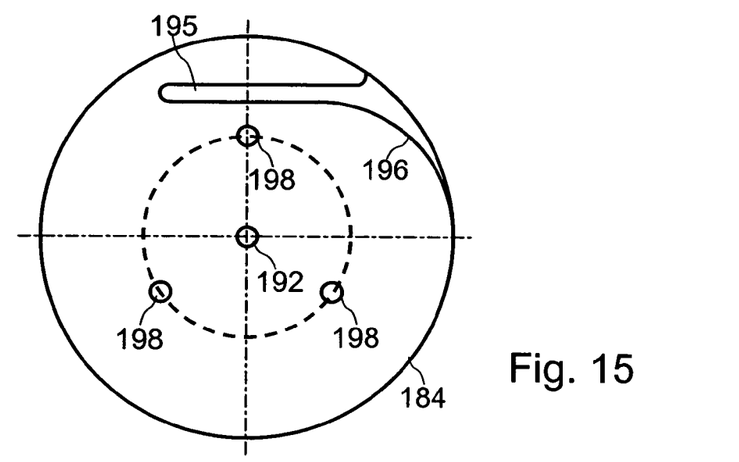
FIGS. 15 and 16 are respectively an axial view and a transverse view of the hub of the drum shown in FIG. 14.
Figure 16:
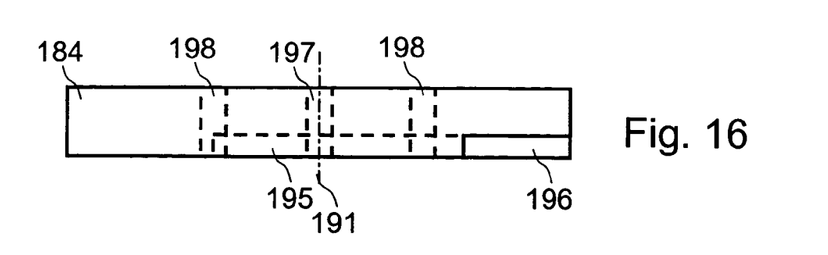

As shown in FIG. 8 and in greater detail in FIG. 9, the pulley 118 drive by the shaft 116 of the servo-motor 114 and actuating the pair of cables 104 & 106 comprises a central core 123 secured to two larger-diameter side plates 121, 122 with circular through orifices being formed in the proximal portions thereof serving to house freely two cylindrical pegs 124, 125 whose central portions are securely fixed to the distal ends of the cables 104, 106.

The pulley 118 is also associated with two cylindrical guide pieces 126 and 127 mounted to rotate freely in two cylindrical orifices formed for this purpose through a distal partition of the housing 112 containing the servo-motor 114 whose shaft 116 drives said pulley. These guide pieces have through orifices along which the cables 104 and 106 slide freely, and they serve as adjustable abutments for the flexible sheaths 108, 110 housing the cables 104 and 106, respectively.

Analogous guidance and abutment devices are associated with the pulley 119 on the shaft 117 of the motor 115 housed in the compartment 113 and actuating the pair of cables 103 & 105.

More precisely, the cylindrical peg 124 freely housed in each of the two circular orifices provided for this purpose in the proximal portions of the side plates 121, 122 associated with the core 123 has a transverse through threaded orifice in which a cylindrical tubular piece 132 is screwed, said piece having a distal channel in which the cable 104 is freely housed, and a proximal channel coaxial therewith and of smaller diameter also serving to receive the cable 104 and having a proximal face which serves as an abutment for an endpiece 130 securely bonded to the distal end of the cable 104.

The cylindrical piece 126 freely housed in a cylindrical orifice formed for this purpose in the distal

What is claimed is:

1. A videoendoscope comprising:
an inspection probe including an inspection tube having a distal endpiece housing an optoelectronic imaging device delivering an electrical signal;
a video processor for processing the electrical signal delivered by the imaging device in order to generate a video signal;
a control unit secured to a proximal end of the inspection tube and provided with controls for controlling and adjusting the video processor;
an umbilical connection cable having a distal end secured to the control unit for connecting the videoendoscope to a light source and to an electrical power supply;
a display unit including a video display screen connected to the video processor in order to display the video signal; and
a bundle of lighting fibers integrated without interruption in the umbilical cable, in the control unit, and then in the inspection tube, and having a distal end housed in the distal endpiece that serves to light a target observed by the probe when a proximal end of the umbilical cable is connected to a light generator;
wherein the display unit is secured to a side face of the control unit to form an assembly configured to be held in one hand and actuated while being held in said hand, the control unit having a control panel on a top face and carrying control members including said controls for controlling and adjusting the video processor, and the assembly being of elongate shape between a distal end and a proximal end so as to be suitable for being held in said hand while allowing the control members to be actuated by using the thumb of said hand;

wherein the video processor is included in the control unit; and wherein the control unit has mechanical and electrical coupling means on both side faces to enable the display unit to be fixed and electrically connected to either side face of the control unit.

2. A videoendoscope according to claim 1, wherein the umbilical cable and the inspection tube are adjacent and connected to the control unit via at least one side face thereof.

3. A videoendoscope according to claim 1, wherein the display unit is secured to the control unit via a hinge enabling the display screen to be tilted about an axis perpendicular to the side face of the control unit, the display unit being electrically coupled to the control unit by means of electrical conductors passing through the hinge.

4. A videoendoscope according to claim 3, wherein the hinge is constituted by a connector providing releasable mechanical and electrical connection between the display unit and the control unit.

5. A videoendoscope according to claim 1, wherein the proximal end of the umbilical cable is secured to a connection unit fitted with connection means for connection to the proximal end of the bundle of lighting fibers and to a light generator, and connection means for connecting the videoendoscope to an electrical power supply.

6. A videoendoscope according to claim 5, wherein the connection endpiece has fixing means for fixing a mechanical adapter to adapt the connection endpiece to the connection endpiece of any light generator, the control panel including a control member for controlling initialization of the video processor as a function of the color temperature of the lamp of the light generator.

7. A videoendoscope according to claim 5, wherein the connection unit further comprises connection means for connecting the probe to a system for processing and or storing images, the videoendoscope further comprising switch means designed to deliver to the video screen either the video signal coming from the video processor or the video signal coming from the system for processing and/or storing images.

8. A videoendoscope according to claim 7, wherein the switch means are integrated in the control unit.

9. A videoendoscope according to claim 7, wherein the switch means are integrated in the display unit.

10. A videoendoscope according to claim 7, wherein the switch means are integrated in the connection unit.

11. A videoendoscope according to claim 7, wherein the connection means for connecting the prove to a system for processing and/or storing images includes a connection pin enabling the videoendoscope to be powered from an electrical power supply associated with the system for processing and/or storing images.

12. A videoendoscope according to claim 7, wherein the connection unit includes means for connecting the videoendoscope to an auxiliary electrical power supply.

13. A videoendoscope according to claim 7, wherein the connection unit includes means for connecting the videoendoscope to an auxiliary video monitor, the switch means including means for sending the video signal applied to the input of the video screen towards the connection means for connection to the auxiliary video monitor.

14. A videoendoscope according to claim 7, further comprising a control handle having means for controlling the switch means.

15. A videoendoscope according to claim 1, wherein the control unit further comprises:

an electromechanical device designed to deform a deformable distal bending section integrated in the distal end of the inspection tube in order to steer the distal end of the inspection tube and thus steer the observation window of the probe, the electromechanical device comprising two motors actuating the distal bending section via two respective pairs of cables for steering the distal end of the inspection tube in two respective planes;

a processor delivering two control signals that are applied respectively to the two motors; and command input means comprising two command input members connected to the processor to input commands intended for the two motors respectively, each of the two command members having a first state in which the processor controls the corresponding motor to keep the orientation of the distal end of the inspection tube fixed, and second and third states in which the processor controls the respective motor to cause the distal end of the inspection tube to vary its orientation respectively in one direction and in the opposite direction.

16. A videoendoscope according to claim 15, wherein each of the motors is of the servo-motor type actuating a pulley coupled to a respective cable pair and of angular position that can be controlled by the respective control signal generated by the processor and applied to the motor, each control signal being in the form of a pulse train, with the width of the pulses corresponding to a determined angular position of the pulley, the processor comprising means for keeping the width of the pulses in each control signal constant so long as the respective control member is in its first state, and for increasing and decreasing the width of the pulses at a predefined speed whenever the corresponding control member is respectively in its second or third state.

17. A videoendoscope according to claim 16, including an additional control member integrated in the control panel and connected to the processor to cause the width of the pulses in the control signals applied to the motors to be controlled in such a manner as to be equal to a middle value corresponding to zero deformation of the distal bending section.

18. A videoendoscope according to claim 17, wherein the additional control member is integrated in the command input means for controlling the distal bending section.

19. A videoendoscope according to claim 15, wherein each of the two command input members comprises a pair of contacts which are both open in the first state, with one or other of the contacts being closed in the second and third states.

20. A videoendoscope according to claim 19, wherein each of the control members comprises two pushbuttons integrated in the control panel to actuate two respective contacts which are in the open state when at rest, and which pass to the closed state when the corresponding pushbutton is held pressed down.

21. A videoendoscope according to claim 15, wherein the means for inputting commands for the bending section comprise a joystick suitable for actuating both command input members simultaneously.

22. A videoendoscope according to claim 15, including an additional control member integrated in the control panel to modify the speed at which the distal end of the inspection tube is steered by selecting a slow speed or a fast speed.

23. A videoendoscope according to claim 15, wherein the processor is programmed to select a fast speed of variation for steering the distal end the inspection tube if at least one of the two control members is maintained in the second or third state for a duration longer than a predefined threshold, and to select a slow speed for varying the steering of the distal end of the inspection tube if both control members are in the first state.

24. A videoendoscope according to claim 15, wherein the processor is programmed to determine the orientation of the distal end of the inspection tube as a function of the form of the control signals applied respectively to two motors, and to display on the display screen symbols representing the determined orientation.

25. A videoendoscope comprising:
an inspection probe including an inspection tube having a distal endpiece housing an optoelectronic imaging device delivering an electrical signal;
a video processor for processing the electrical signal delivered by the imaging device in order to generate a video signal;
a control unit secured to a proximal end of the inspection tube and provided with controls for controlling and adjusting the video processor;
an umbilical connection cable having a distal end secured to the control unit for connecting the videoendoscope to a light source and to an electrical power supply;
a display unit including a video display screen connected to the video processor in order to display the video signal;
switch means designed to deliver to the video screen either the video signal coming from the video processor or the video signal coming from a system for processing and/or storing images; and
a bundle of lighting fibers integrated without interruption in the umbilical cable, in the control unit, and then in the inspection tube, and having a distal end housed in the distal endpiece that serves to light a target observed by the probe when a proximal end of the umbilical cable is connected to a light generator;
wherein the display unit is secured to a side face of the control unit to form an assembly configured to be held in one hand and actuated while being held in said hand, the control unit having a control panel on a top face and carrying control members including said controls for controlling and adjusting the video processor, and the assembly being of elongate shape between a distal end and a proximal end so as to be suitable for being held in said hand while allowing the control members to be actuated by using the thumb of said hand;
wherein the proximal end of the umbilical cable is secured to a connection unit fitted with connection means for connection to the proximal end of the bundle of lighting fibers and to a light generator, and connection means for connecting the videoendoscope to an electrical power supply;
wherein the connection unit further comprises connection means for connecting the probe to the system for processing and or storing images; and wherein the control unit has means for controlling a system for processing and/or storing images, which system is connected to the connection means of the connect unit, said connection means including a pin for transmitting the video signal generated by the video processor to a video input of the system for processing and/or storing images, a pin for transmitting to the switch means a video signal generated by the system for processing and/or storing images, and a pin for connecting the controls of the control unit to a control interface of the system for processing and/or storing images.

26. A videoendoscope comprising:
an inspection probe including an inspection tube having a distal endpiece housing an optoelectronic imaging device delivering an electrical signal;
a video processor for processing the electrical signal delivered by the imaging device in order to generate a video signal;
a control unit secured to a proximal end of the inspection tube and provided with controls for controlling and adjusting the video processor;
an umbilical connection cable having a distal end secured to the control unit for connecting the videoendoscope to a light source and to an electrical power supply;
a display unit including a video display screen connected to the video processor in order to display the video signal; and
a bundle of lighting fibers integrated without interruption in the umbilical cable, in the control unit, and then in the inspection tube, and having a distal end housed in the distal endpiece that serves to light a target observed by the probe when a proximal end of the umbilical cable is connected to a light generator;
switch means designed to deliver to the video screen either the video signal coming from the video processor or the video signal coming from the a system for processing and/or storing images; and
means for controlling the switch means to direct the video signal coming from the system for processing and/or storing images to the video screen immediately said system is connected to the connection means;
wherein the display unit is secured to a side face of the control unit to form an assembly configured to be held in one hand and actuated while being held in said hand, the control unit having a control panel on a top face and carrying control members including said controls for controlling and adjusting the video processor, and the assembly being of elongate shape between a distal end and a proximal end so as to be suitable for being held in said hand while allowing the control members to be actuated by using the thumb of said hand;
wherein the proximal end of the umbilical cable is secured to a connection unit fitted with connection means for connection to the proximal end of the bundle of lighting fibers and to a light generator, and connection means for connecting the videoendoscope to an electrical power supply; and
wherein the connection unit further comprises connection means for connecting the probe to a system for processing and or storing images.

27. A videoendoscope comprising:
an inspection probe including an inspection tube having a distal endpiece housing an optoelectronic imaging device delivering an electrical signal;
a video processor for processing the electrical signal delivered by the imaging device in order to generate a video signal;
a control unit secured to a proximal end of the inspection tube and provided with controls for controlling and adjusting the video processor;
an umbilical connection cable having a distal end secured to the control unit for connecting the videoendoscope to a light source and to an electrical power supply;

a display unit including a video display screen connected to the video processor in order to display the video signal; and a bundle of lighting fibers integrated without interruption in the umbilical cable, in the control unit, and then in the inspection tube, and having a distal end housed in the distal endpiece that serves to light a target observed by the probe when a proximal end of the umbilical cable is connected to a light generator;

a storage and transport case containing an electrical power supply and lighting generator, the storage case containing a drum around which the probe can be wound, the drum being mounted in such a manner as to be capable of turning freely about its axis and having a tubular cavity for receiving the distal end of the probe, and opening out tangentially from the cylindrical surface of the drum;

wherein the display unit is secured to a side face of the control unit to form an assembly configured to be held in one hand and actuated while being held in said hand, the control unit having a control panel on a top face and carrying control members including said controls for controlling and adjusting the video processor, and the assembly being of elongate shape between a distal end and a proximal end so as to be suitable for being held in said hand while allowing the control members to be actuated by using the thumb of said hand.

28. A videoendoscope according to claim 27, wherein the drum comprises a central hub held between two side plates on the same axis, the cavity being made from one of the side faces of the hub and being closed latterly by one of the two side plates.

29. A videoendoscope according to claim 28, wherein the central hub is made of a hard cellular foam.

30. A videoendoscope according to claim 27, wherein the central hub is made of a material presenting a high coefficient of friction.

31. A videoendoscope according to claim 27, wherein the storage case has a housing in which the drum is secured, the housing possessing an opening giving access to a portion of the cylindrical surface of the drum.

32. A videoendoscope according to claim 27, wherein the case has a lid whose inside face is covered in foam, the drum being mounted in the case in such a manner as to be prevented from rotating by the foam in the lid when the, lid is closed on the case.

33. A videoendoscope according to claim 27, wherein the inside diameter of the cylindrical cavity is slightly greater than the greatest diameter of the distal end of the probe that is to be wound about the drum.

* * * * *